United States Patent [19]

Davis et al.

[11] 4,350,661
[45] Sep. 21, 1982

[54] METHOD AND APPARATUS FOR ANALYZING SUPERSONIC FLOW FIELDS BY LASER INDUCED FLUORESCENCE

[75] Inventors: Steven J. Davis; Nazareno L. Rapagnani, both of Albuquerque, N. Mex.

[73] Assignee: The United States of America as represented by the Secretary of the Air Force, Washington, D.C.

[21] Appl. No.: 110,889

[22] Filed: Jan. 10, 1980

[51] Int. Cl.³ .................... G01N 21/63; G01N 3/091; G01N 31/00

[52] U.S. Cl. ................................ 422/98; 23/232 E; 73/147; 250/302; 250/458.1; 372/59; 372/58

[58] Field of Search ................. 250/302, 458; 73/147, 73/116; 422/98, 52; 23/232 E; 331/94.5 D, 94.5 G

[56] References Cited

U.S. PATENT DOCUMENTS

| | | | |
|---|---|---|---|
| 2,952,776 | 9/1960 | Schumacher et al. | 73/147 |
| 3,688,215 | 8/1972 | Spencer et al. | 331/94.5 |
| 3,982,208 | 9/1976 | Camac | 331/94.5 G |
| 4,048,586 | 9/1977 | Witte et al. | 331/94.5 D |
| 4,095,193 | 6/1978 | Clark | 331/94.5 G |
| 4,148,612 | 4/1979 | Taylor et al. | 422/98 X |
| 4,150,951 | 4/1979 | Capelle et al. | 422/98 X |
| 4,188,120 | 2/1980 | McDonald et al. | 250/458 X |

OTHER PUBLICATIONS

Continuous Wave Chemical Laser for Laser-Induced Fluorescence Studies, R. R. Stevens and T. A. Cool, The Review of Scientific Instruments, vol. 42, No. 10 (Oct. 71), pp. 1489–1494.

*Primary Examiner*—Michael S. Marcus
*Attorney, Agent, or Firm*—Donald J. Singer; Thomas L. Kundert

[57] ABSTRACT

A method and apparatus for visually analyzing gaseous flow fields. A vaporous substance that fluoresces when irradiated by a particular laser beam is injected into a structure containing a flowing gas in a manner such that a uniform dispersion of the vaporous substance throughout the gas flow is achieved. The beam from a pump laser in optical communication with the gas flow pumps the ground state of the vaporous substance to an excited state and causes the vaporous substance to fluoresce in the area illuminated by the beam, thus providing a visual indication of the pattern of gas flow in the structure.

4 Claims, 2 Drawing Figures

METHOD AND APPARATUS FOR ANALYZING SUPERSONIC FLOW FIELDS BY LASER INDUCED FLUORESCENCE

STATEMENT OF GOVERNMENT INTEREST

The invention described herein may be manufactured and used by or for the government for governmental purposes without the payment of any royalty thereon.

BACKGROUND OF THE INVENTION

This invention relates generally to the analysis of both supersonic and subsonic flowing gases, and in particular it relates to the analysis of flow fields in supersonic gas lasers such as hydrogen fluoride (HF) or deuterium fluoride (DF) chemical lasers.

Chemical lasers are efficient lasers, having great average power capabilities and other advantageous characteristics such as the ability to produce laser power from a reaction of gases that are easily bottled. These advantages have made the chemical laser the subject of much study and investigation, but these efforts have been hampered by a lack of any precise method for analyzing the mixing reacting flow fields in such lasers. The efficiency of chemical lasers is controlled in large part by the mixing of the reactant gases. Accurate, visual mappings of the flow fields are critically needed to form a data base for theoretical modeling and to improve mixing efficiencies.

The typical diagnostic approach used in the past to analyze laser flow fields has been to observe the visual chemiluminescence of HF or DF overtone emission. This approach suffers from the fact that the chemiluminescence is not well localized and spatial resolution is lost. For example, in order to observe the visible emission originating from the gases in the middle of a typical laser nozzle bank due to chemiluminescence, you must look through the emission from gases flowing between the viewer and the area being investigated. It is apparent that this would obscure observations and make interpretations more difficult and subject to error.

SUMMARY OF THE INVENTION

The present invention is an improvement which largely eliminates the problems of the prior art. This is accomplished by seeding a suitable vaporous substance such as molecular iodine into the gas flow and then irradiating the area of the gas flow to be examined with a suitable laser such as an argon ion laser. The invention was made with the specific purpose in mind of analyzing the mixing reacting flow fields in HF/DF chemical lasers but the invention would have application in analyzing the operation and efficiency of any device employing mixing or laminar flow fields. The invention provides a very sensitive diagnostic for determining if gases are flowing properly through a laser nozzle. Other species that fluoresce, such as sodium vapor, can be used as the seed gas. Sodium vapor fluoresces when pumped by a dye laser. It would be possible by using several fluorescing vapor species having differing masses, to determine the effect the molecular mass of a species has on the efficiency with which it mixes with other flowing gases. The argon laser beam employed to pump the molecular iodine is less than 1 mm in diameter. Thus, a very small portion of a flow field can be selected for analysis and high spatial resolution of the flow field can be obtained.

Accordingly, an object of this invention is to provide as effective visual mapping technique for flowing gases.

Another object of the invention is to selectively observe extremely localized regions in a reacting gas flow so as to obtain high spatial resolution of the flow field.

Other objects and advantages of the invention will become apparent to those skilled in this art when considering the following detailed description and the referenced drawing.

DETAILED DESCRIPTION OF THE INVENTION

Figure 1:
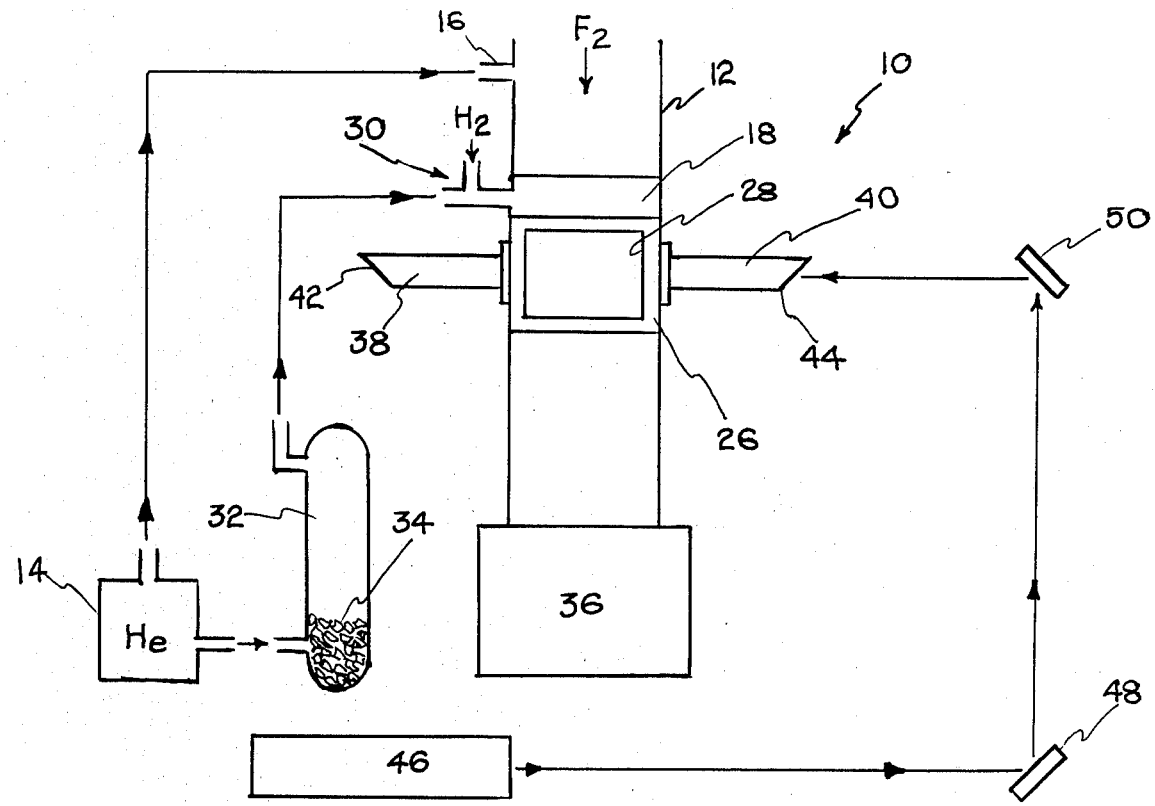
FIG. 1 is a schematic illustration of the invention applied to an HF chemical laser.

Referring now to FIG. 1 of the drawing, chemical laser 10 includes a suitable supply section 12 containing an oxidizing gas such as fluorine, $F_2$, obtained from a suitable source (not shown). Typically supply section 12 can be a combustor supplied with gases that are hypergolic and react to form fluorine atoms. It has been determined that the addition of measured quantities of an inert buffer gas such as helium improves the lasing reaction. Helium (He) from source 14 is added to the gas mixture in supply section 12 via conduit 16.

Figure 2:
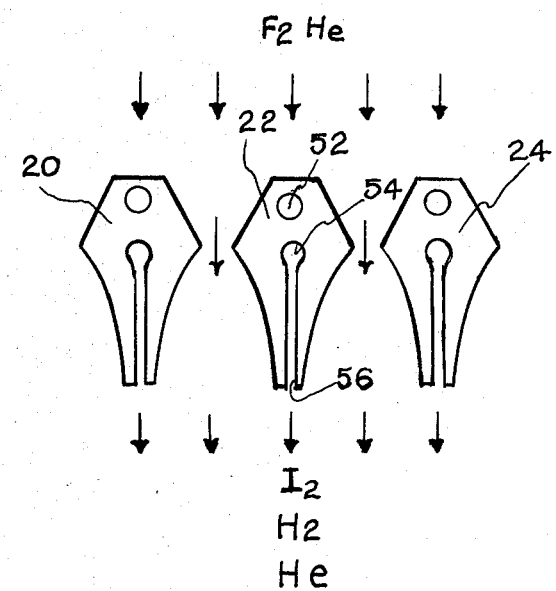
FIG. 2 is an enlarged view of typical nozzle elements employed in a nozzle bank of a HF chemical laser.

The laser includes a nozzle section 18 that receives a gas flow from section 12. The nozzle section of a typical laser would include a large number of nozzle elements to form a nozzle bank, but only a representative number of nozzle elements 20, 22 and 24 are shown in FIG. 2 of the drawing. Nozzle section 18 would include considerable internal manifolding to accomplish the gas flow distribution that will be discussed hereafter. However, since such manifolding is state of the art technology, it will not be shown or described in complete detail herein. Lasing section 26, which includes an optical cavity wherein the lasing reaction takes place is positioned immediately downstream of nozzle section 18. The various optical components that forms the optical cavity for the laser, and extracts the laser beam therefrom, will not be described since they are known in the art and are not a part of the present invention. Section 26 is provided with a viewing window 28 through which the gas flow can be visually observed or photographed. A fuel gas such as hydrogen, $H_2$, from a suitable source (not shown) is supplied to the nozzle section via conduit 30 where it is added to the oxidizer gas to form a reacting gas mixture in lasing section 26.

An inert buffer gas such as helium is also normally added to the fuel gas for the purpose of improving the laser reaction. Helium gas from source 14 is passed through a container 32 containing iodine $I_2$, crystals 34 at room temperature. The He is seeded with $I_2$ vapor. Thereafter the $HeI_2$ mixture is added to the fuel gas $H_2$ prior to entry into the nozzle section. A scrubber device 36 of a suitable type is located downstream of the lasing cavity to receive the exhaust therefrom. The exhaust from an HF or DF chemical laser contains an acid that can be removed by several known methods.

Housings 38 and 40 having Brewster's angle end windows 42 and 44 are shown mounted in a position such that their longitudinal axes coincides with the optical axis of the HF laser. The purpose of the housings are to give optical access to the lasing cavity. It should be understood that similar access could be obtained to other parts of the laser if desired. An argon ion laser 46 is mounted adjacent chemical laser 10 and the output beam from laser 46 is directed down the optical axis of laser 10 by mirrors 48 and 50.

Referring to FIG. 2 where it can be seen that the fluorine gas is expanded through converging diverging supersonic nozzles formed by nozzle elements 20, 22 and 24. Only one nozzle element will be described in detail, but all would be substantially identical. Nozzle element 22 includes a passageway 52 for a suitable coolant and a passageway 54 for the hydrogen fuel gas supplied to the nozzle means. A channel 56 extends from passageway 54 to the exit area of the nozzle bank for adding the hydrogen gas into the flowing fluorine gas. The two gases mix and react in the optical cavity.

The effectiveness of the invention was first tested with the argon laser 46 running, single frequency, single mode, at 5145 A. The iodine vessel (two liter) was at room temperature and helium from source 14 was flowing through the iodine crystals to the nozzle section. No hydrogen or fluorine gas were used in this test. The argon laser beam effeciently pumped the ground state of the molecular iodine $I_2$ to the $\beta^3\pi(0v+)$ state and visible $I_2$ (B−X) emission was observed through viewing window 28. Laser induced emission on the visible $I_2$(B−X) emission was observed.

When laser 10 is run in the hot flow mode, the $I_2$ in the fuel gas reacts with F+ atoms and IF is formed. However, the argon laser optically pumps IF $\beta^3\pi(0+)$ and visible fluorescence can be observed in the IF. Such fluoresence was observed with the chemical laser running in the hot flow mode and all gas flows turned on.

While the invention has been described by reference to a particular embodiment, it should be understood that modifications and other applications of the invention will be apparent to those skilled in the field of technology of the invention.

What is claimed is:

1. An apparatus for visually analyzing mixing efficiencies in a gas laser comprising:

a supply section means for providing a flow of oxidizing gases;

mixing nozzle means connected to said supply section for receiving and directing the flowing oxidizing gases provided by said supply section;

fuel supply means connected to said mixing nozzle means for supplying fuel gas to said mixing nozzle means, whereby the fuel gas is directed out of said mixing nozzle means along with said oxidizing gas, gas injection means connected to said fuel supply means for injecting a suitable vaporous substance into the fuel gas flow from said fuel supply means for mixing therewith, optical cavity means connected to said mixing nozzle means for receiving the mixing gases exhausted by said mixing nozzle means, window means mounted on said optical cavity means for visually observing the gas flow in said optical cavity means, and, a pump laser means mounted adjacent said optical cavity means and in optical communication with the interior of said optical cavity means for irradiating a selected portion of the flowing gases to cause a visible fluorescence of the vaporous substance in that portion of the gas flow irradiated by said laser to provide a visible indication of the mixing occurring between said oxidizing gas and said fuel gas in the irradiated portion.

2. The apparatus recited in claim 1 wherein the vaporous substance is molecular iodine and said pump laser means is an argon ion laser.

3. The apparatus recited in claim 2 wherein said oxidizing gas is fluorine and helium, and said fuel gas is hydrogen and helium.

4. The apparatus recited in claim 3 wherein said gas injection means includes a source of helium gas connected to said fuel supply means by conduit means, and a container of iodine crystals mounted intermediate the ends of said conduit whereby helium gas flowing from said helium source to said fuel supply means is seeded with molecular iodine vapor as it passes through said container of iodine crystals.

* * * * *